(12) United States Patent
van der Linden

(10) Patent No.: US 6,994,685 B2
(45) Date of Patent: Feb. 7, 2006

(54) METHOD AND A DEVICE FOR CREATING A PROTECTING ATMOSPHERE

(75) Inventor: Jan van der Linden, Saltsjöbaden (SE)

(73) Assignee: Cardia Innovation AB, Saltsjobaden (SE)

( * ) Notice: Subject to any disclaimer, the term of this patent is extended or adjusted under 35 U.S.C. 154(b) by 400 days.

(21) Appl. No.: 10/149,931

(22) PCT Filed: Dec. 19, 2000

(86) PCT No.: PCT/SE00/02579

§ 371 (c)(1),
(2), (4) Date: Oct. 7, 2002

(87) PCT Pub. No.: WO01/45790

PCT Pub. Date: Jun. 28, 2001

(65) Prior Publication Data

US 2003/0060750 A1 Mar. 27, 2003

(30) Foreign Application Priority Data

Dec. 21, 1999 (SE) .............................. 9904699

(51) Int. Cl.
*A61M 37/00* (2006.01)

(52) U.S. Cl. .......................................... 604/26
(58) Field of Classification Search ............ 128/200.14, 128/200.24; 604/26, 27; 219/72; 43/124
See application file for complete search history.

(56) References Cited

U.S. PATENT DOCUMENTS

| 3,632,950 A | * | 1/1972 | Berghof ........................ 219/72 |
| 5,394,643 A | * | 3/1995 | Schmittmann ................ 43/124 |
| 5,458,135 A | * | 10/1995 | Patton et al. .......... 128/200.14 |
| 5,660,172 A | * | 8/1997 | Hatton ................... 128/205.54 |
| 6,241,751 B1 | | 6/2001 | Morgan et al. | |

FOREIGN PATENT DOCUMENTS

| DE | 26 46 710 | 4/1978 |
| FR | 2 656 218 | 6/1991 |
| WO | WO 97/26034 | 7/1997 |
| WO | WO 99/29249 | 6/1999 |

* cited by examiner

*Primary Examiner*—George Manuel
(74) *Attorney, Agent, or Firm*—Greer, Burns & Crain, Ltd.

(57) ABSTRACT

The invention refers to a method for creating a protecting atmosphere in a volume, including the steps of: providing a device, which is arranged to permit the supply of a gas and which includes at least a supply conduit including a discharge end and a porous body provided at said discharge end, supplying said gas by means of said device through the porous body in such a way that a controlled flow of said gas is formed and providing said porous body in relation to said volume in such a way that the controlled gas flow forms a gas cushion, which substantially fills said volume, and that said gas cushion is arranged to prevent air from the environment from reaching said volume. The invention also refers to a device for creating a protecting atmosphere in a volume.

25 Claims, 2 Drawing Sheets

METHOD AND A DEVICE FOR CREATING A PROTECTING ATMOSPHERE

THE BACKGROUND OF THE INVENTION AND PRIOR ART

The present invention refers to method for creating a protecting atmosphere in a volume. The invention also refers to a device for creating a protecting atmosphere in a volume.

During operations which are performed in an open manner, i.e. when an inner portion of the body is uncovered for the performance of the surgical operation, it may be important to prevent air from the environment from reaching the open portion of the body in order to avoid, interalia, infections caused by micro-organisms and bacteria, which are always present in the surrounding air and which are falling down towards the open portion of the body. Consequently, it is desirable to create a protecting atmosphere around said open portion for protecting said portion from non-sterile air and falling particles. In addition, different surgical operations may have various requirements on the protecting atmosphere. In this connection reference is made to WO, A1, 99/29249.

One problem which may arise in connection with the creation of a protecting atmosphere around for instance a temporarily open, inner portion of a human being, which has been open in order to perform a surgical operation, is to avoid the formation of turbulence when creating said protecting atmosphere and thus the mixing of air from the environment into said protecting atmosphere.

Today instruments and tools to be used in connection with for instance an operation to be performed on a human being, are sterilised in order to obtain a complete killing of micro-organisms, including bacteria, which otherwise may be transferred to the human being in question and cause infections. Such a sterilising may be performed by means of any type of heat treatment, for instance in an autoclave, radiation or by chemical substances. However, there is a risk that micro-organisms and bacteria present in the surrounding air may be transferred to said sterilised instruments and tools during use, especially when they have been contaminated by blood, wherein these in the next step may be transferred to the human being subjected to the operation.

SUMMARY OF THE INVENTION

The object of the present invention is to provide a method and a device for creating a protecting atmosphere in a volume, which for instance may adjoin an outwardly open, inner portion of the body of a human being or an animal without air from the environment being mixed into said atmosphere.

This object is obtained by the method initially defined, which includes the steps of: providing a device, which is arranged to permit the supply of a gas and which includes at least one supply conduit including a discharge end and a porous body provided at said discharge end, supplying said gas by means of said device through the porous body in such a way that a controlled flow of said gas is formed, and providing said porous body in relation to said volume in such a way that the controlled gas flow forms a gas cushion, which substantially fills said volume, wherein said gas cushion is arranged to prevent air from the environment from reaching said volume. The advantage of letting the gas passing through a porous body is that the cavities of the porous body, which are a great number and positioned very closely to each other and which function as supply nozzles, distribute the gas in thin layers lying close to each other and forming, when the gas leaves the porous body, a substantially laminar continuous gas flow, which enables the formation of a gas cushion. The porous body also slows down the gas passing said supply conduit, wherein a slow, substantially laminar, continuous gas flow is obtained. The gas cushion, which hereby is formed, prevents the surrounding air from reaching the volume filled by the gas cushion and thus also bacteria and other particles which may be present in the surrounding air. In addition, said gas cushion is formed in a controlled manner, wherein the problems connected to turbulence are minimised.

According to an embodiment of the invention, the porous body is manufactured in a foam rubber like material. The advantage of foam rubber-like materials is partly that they include a large number of open cells functioning as supply nozzles to the gas and partly that they are inexpensive and light. A material, which has a low weight, may be very valuable in certain applications which will be mentioned later in the description. In addition, said porous body is intended to function as a disposable product, wherein an inexpensive material is preferable.

According to a further embodiment of the invention, the porous body has such a design that the gas propagates in several directions from the body. Since the gas propagates in several directions, the arrangement of the porous body in relation to said volume is made easier.

According to a further embodiment of the invention, said porous body includes a homogenous body having a hole arranged to receive an end portion of said supply conduit, which end portion includes said discharge end. Said homogenous body may have various shapes, for instance a spherical shape, which may be advantageous in order to obtain a gas propagation in all directions, wherein the porous body may be provided in an arbitrary manner in relation to said volume and form said gas cushion.

According to further embodiment of the invention, said hole extends to a point located substantially centrally in said homogenous body. According to a preferred embodiment, said hole has a diameter which substantially corresponds to the diameter of said end portion of said supply conduit. Preferably, the diameter of said hole corresponds substantially the diameter of said end portion of the supply conduit, wherein said hole may be arranged to enclose said end portion of the supply conduit in such a way that said end portion is maintained in said hole by means of friction.

According to a further embodiment of the invention, said porous body has a small size in relation to said volume. It is very advantageous to give the porous body a small size in relation to the volume to be protected from penetration of surrounding air especially in the applications where said volume adjoins a temporarily outwardly open, inner portion of the body of a human being or an animal. Hereby, it is possible to let the porous body abut a part of said outwardly open, inner portion, which part merely needs to contain a fraction of said outwardly open, inner portion. Hereby, the performance of for instance a surgical operation is enabled with said porous body present and without the porous body being blocking to a too large extent. Preferably, the porous body is manufactured in a foam rubber material, which is advantageous due to the fact that it has a low weight and thus does not exert any injuring pressure against the part which it abuts. Such a porous body may, in addition, in the applications where the volume adjoins a temporarily outwardly open, inner portion of the body of a human being or an animal, float on the blood in the portion. The device may therefore be positioned in an easy manner in a blood-filled portion. Furthermore, it has been proved, in connection with trials which have been performed, that the gas merely propagates from the porous body in the directions where the body does not abut blood.

According to a further embodiment of the invention, said volume is defined by the porous body, wherein the porous body may form the shape of a container. Said container may have a dimension which makes it possible to place for instance an instrument or a tool to be used in connection with a surgical operation in said container, and which during use, especially when it has been contaminated by blood, should not come into contact with the surrounding air. In order to ensure that the gas cushion fills the volume defined by the porous body, the device may include means arranged to distribute the gas in said porous body. Said means may for instance include a plurality of supply conduits having orifices in said porous body.

According to a further embodiment of the invention the main component of the gas is carbon dioxide. In the applications where a protecting atmosphere is to be created in a volume adjoining an outwardly open inner portion of the body of a human being or an animal, it is advantageous that the gas includes carbon dioxide due to the fact that carbon dioxide has a high solubility in the tissue of said body in relation to oxygen and nitrogen. In addition, carbon dioxide has at least a bacteriostatic function, which reduces the growth of bacteria and/or other microorganisms, which possibly may be present in the open portion. In this connection, reference is again made to WO, A1, 99/29249. Furthermore, carbon dioxide is heavier than air, wherein a protecting atmosphere in said volume adjoining an outwardly open, inner portion of for instance a human being may be created in an easy manner. It is to be noted that said gas may be supplied to said volume in a continuous flow, wherein it is possible to ensure that the surrounding air is prevented from reaching said volume even if a part of the supplied gas leaves the area. Another possibility is, at least initially, to supply gas continuously in order to create said gas cushion, whereafter gas is supplied periodically in order to maintain said gas cushion. The device may be combined by a gas sensing member, which is arranged to sense to concentration of the supplied gas or air in said volume. By means of such a sensing, the gas supply to the actual volume may be controlled in such a way that if an increased air concentration is noted, the gas supply is also increased, or if the air concentration in the actual volume exceeds a predetermined level the gas supply is increased. It should also be noted that said gas may include oxygen, for instance in the cases when said tissue of said open body portion is strongly oxygen dependent. Oxygen, as well as carbon dioxide, is heavier than air, wherein the protecting atmosphere in said volume may be created in an easy manner since the heavier gas will pass downwardly in the open body portion and force away the non-sterile air present in the lower part of this open portion. In this connection it is also to be mentioned that when creating a protecting atmosphere in a volume adjoining an outwardly open inner portion of the body of a human being or an animal, it is also possible to add a medicament together with the gas. By adding medicaments together with the gas through the porous body a homogeneous propagation of the medicament is obtained. The supply of medicaments may take place continuously or intermittently. In addition, the gas supplied maybe conditioned, i.e. humidified and/or cooled down or heated.

According to a further embodiment of the invention, the gas includes air. In certain applications a protecting atmosphere including sterile air may be satisfactory. The main thing is that air from the environment, i.e. non-sterile air, is prevented from reaching said volume.

The object is also obtained by the device initially defined, which is characterised in that the porous body is arranged to supply said gas to the volume in a controlled flow in order to enable the formation of a gas cushion intended to fill substantially said volume and thus prevent air from this environment from reaching said volume.

Advantageous embodiments of the device are defined in the dependent claims 18–25.

BRIEF DESCRIPTION OF THE DRAWINGS

The present invention is now to be described more closely by means of different embodiments and with reference to the drawings attached, in which FIG. 1 discloses a schematic view of a device according to a first embodiment of the invention for creating a protecting atmosphere in a volume adjoining a temporarily open, inner portion of the human being, FIG. 2a discloses a part of the device according to FIG. 1 with a porous body with a substantially spherical shape, which is positioned in a temporarily open, inner portion of a human being, wherein said portion is disclosed in a sectional view, FIG. 2b discloses a part of the device according to FIG. 1, with a porous body with a substantially cubic shape, which is positioned in a temporarily open, inner portion of a human being, wherein said portion is disclosed in a sectional view, FIG. 3 discloses schematically a sectional view of a porous body in the form of a cylinder, FIG. 4 discloses a schematic view of a device according to a second embodiment of the invention, FIG. 5 discloses a schematic sectional view of a device according to said first embodiment for creating a protecting atmosphere in a volume in which a sterilised instrument is present.

DETAILED DESCRIPTION OF DIFFERENT EMBODIMENTS OF THE INVENTION

Elements having substantially the same function have been provided with the same reference signs in the various figures.

Figure 1:
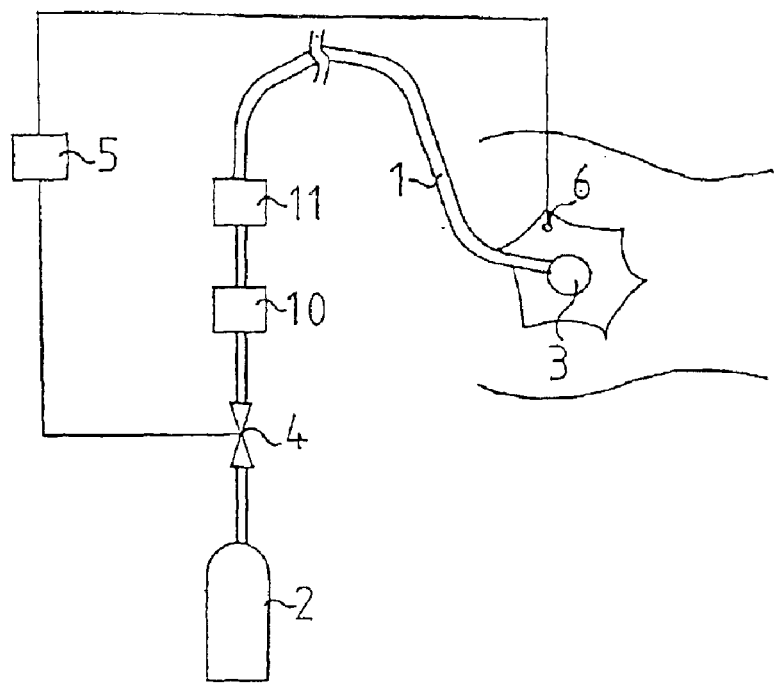
Figure 2A:
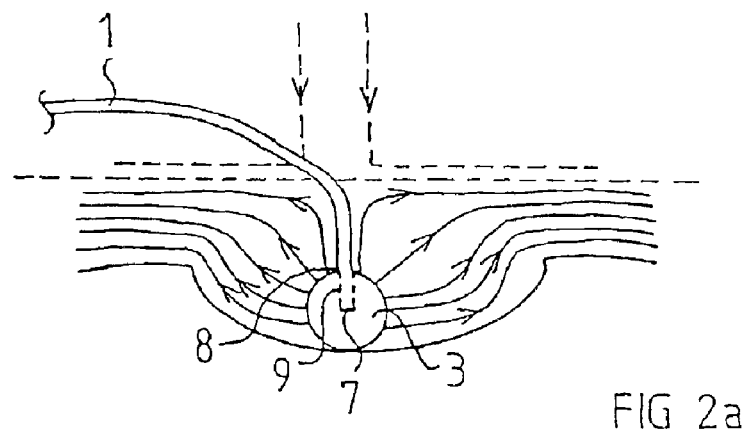
Figure 2B:
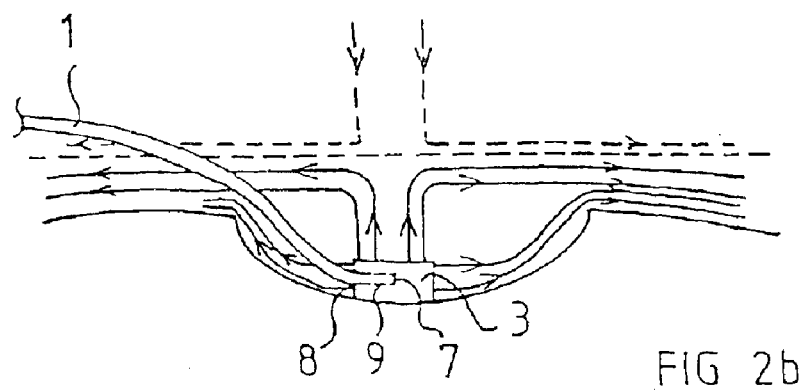

FIG. 1, FIG. 2a and FIG. 2b disclose a device according to a first embodiment of the invention for creating a protective atmosphere in a volume adjoining a temporarily open, inner portion of a human being in order to prevent air from the environment from reaching the volume. Such an open portion is formed during operations performed openly, i.e. when an inner portion of the body is uncovered for performing of the surgical operation. In connection with for instance heart operations, a substantial part of the interior of the thorax is uncovered so that this in normal cases has direct contact with the surrounding atmosphere, i.e. with air.

The device includes a supply conduit 1 in the form of a thin and flexible hose which is connectable to a gas source 2 and a porous body 3. The gas, which preferably is substantially sterile, is arranged to be supplied to the volume through the porous body 3 in a controlled flow in order to enable the formation of a gas cushion intended to fill substantially the actual volume and thus prevent air from the environment from reaching the volume. In addition, the device includes a valve member 4 by which the gas supplied to porous body 3 is controllable. In the example disclosed, the valve member 4 is controlled by means of the control unit 5 connected to the valve member 4. The control unit 5 may in its turn be connected to a gas sensing member 6, which is arranged to sense the concentration of the gas supplied or the concentration of the air in the actual volume. By means of such a sensing, the gas supplied to the volume may be controlled in such a way that if an increased air concentration is noted, also the gas supply is increased, or if the air concentration in the area exceeds a predetermined level, the gas supply is increased.

The porous body is thus arranged to supply the gas in a controlled flow in order to enable the formation of said gas cushion. Preferably, the porous body 3 is manufactured in a foam rubber-like material having a large number of open cells, which are provided closely to each other and which function as supply nozzles distributing the gas in thin layers lying close to each other. The layers form, when the gas leaves the porous body, a substantially laminar, continuous gas stream enabling the formation of the gas cushion. The porous body 3 is totally manufactured in said foam rubber-like material and thus forms a homogenous foam rubber body 3.

As appears from FIG. 2a and FIG. 2b, the supply conduit 1 includes a discharge end 7 and the porous body 3 a hole 8. The hole 8 extends to a point located substantially centrally in the homogeneous porous body 3. The hole 8, which is arranged to receive an end portion of the supply conduit 1, that includes the discharge end 7, and which is arranged to enclose the end portion 9, has a diameter which is somewhat less than the diameter of the end portion 9, wherein the end portion 9 is maintained in the hole 8 by means of friction. The continuous arrows in FIG. 2a and FIG. 2b indicate the gas flow from the porous body 3, wherein the gas includes a gas which is heavier than the surrounding air. The dotted arrows indicate how the surrounding air is prevented from reaching the volume filled by the gas cushion.

The porous body 3 may have various shapes. FIG. 2a discloses a porous body 3 having a spherical shape, which has the advantage that a gas propagation is obtained in all directions, wherein the porous body 3 may be located arbitrarily in relation to said volume. FIG. 2b discloses a porous body 3 having a cubic shape. Also this shape offers a gas propagation in several directions, wherein it may be located in several manners in relation to the actual volume.

Preferably, the porous body 3 has such a size that it merely occupies a fraction of the volume adjoining the outwardly open portion of the body. Hereby, the porous body 3 may advantageously be located in the open portion of the body in such a way that it abuts a part of said outwardly open portion. In addition, by locating the porous body 3 in the open portion, preferably in a lower part of the open portion as is disclosed in FIG. 2a and FIG. 2b, the possibilities that air from the environment reaches the volume adjoining the open portion are minimised. Due to the facts that the porous body 3 is manufactured of a foam rubber-like material and thus has a low weight and that it has such a shape that it offers a gas propagation in several directions in combination with the fact that the supply conduit 1 includes a thin, flexible hose, the porous body 3 may easily be moved within the outwardly open portion of the body without exerting any injuring pressure against the part it abuts and maintain said gas cushion.

It is to be noted that the temperature of the gas may be controlled and/or that the gas may be humidified by water or water steam by means of a conditioner member 10 before it is supplied to the actual volume in order to prevent the open portion of the body from drying. Thus, it is also possible to cool down the gas to a temperature which is somewhat lower than the surrounding air before the gas is supplied to the actual volume. The cooling has the advantage that the gas thanks to its lower temperature obtains a higher density and consequently becomes heavier. In such a way the gas may easier force away the surrounding air in the actual volume. It is also to be noted that a medicament may be supplied together with the gas, wherein the device may include a container 11 including the medicament. However, it is also possible to heat the gas before it is supplied to the volume. The advantage of heating the gas is the body temperature of the patient may be maintained, wherein certain body functions will function more appropriately.

Figure 3:
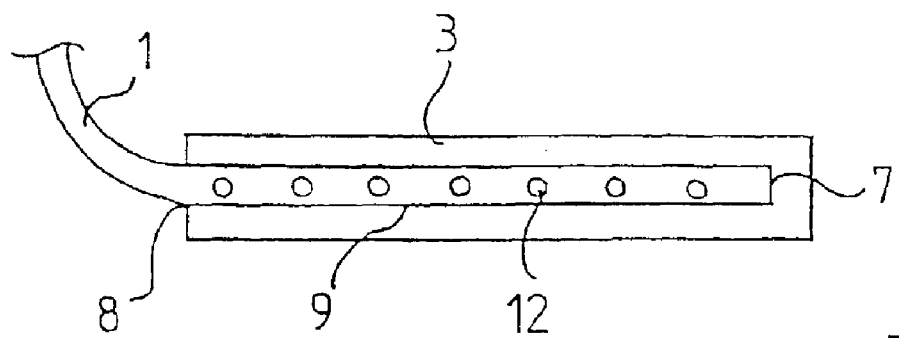

FIG. 3 discloses a porous body 3 having an elongated cylindrical shape, which may have a circular cross-section or a polygonal, for instance a rectangular cross-section. As the porous bodies 3 disclosed in FIG. 2a and FIG. 2b, the porous body 3 includes a hole 8 arranged to receive an end portion 9 including a discharge end 7 of the supply conduit 1. In contrast to the holes 8, which are disclosed in FIG. 2a and FIG. 2b, the hole 8 of the cylindrical porous body 3 extends along substantially the whole length of the cylindrical porous body 3, wherein the hole 8 of this body may receive a substantially longer end portion 9 of the supply conduit 1. In order to obtain a gas propagation along the whole length of the cylindrical body 3, the end portion 9 includes a plurality of discharge outlets 12, which are uniformly distributed along the length of the end portion 9.

Figure 4:
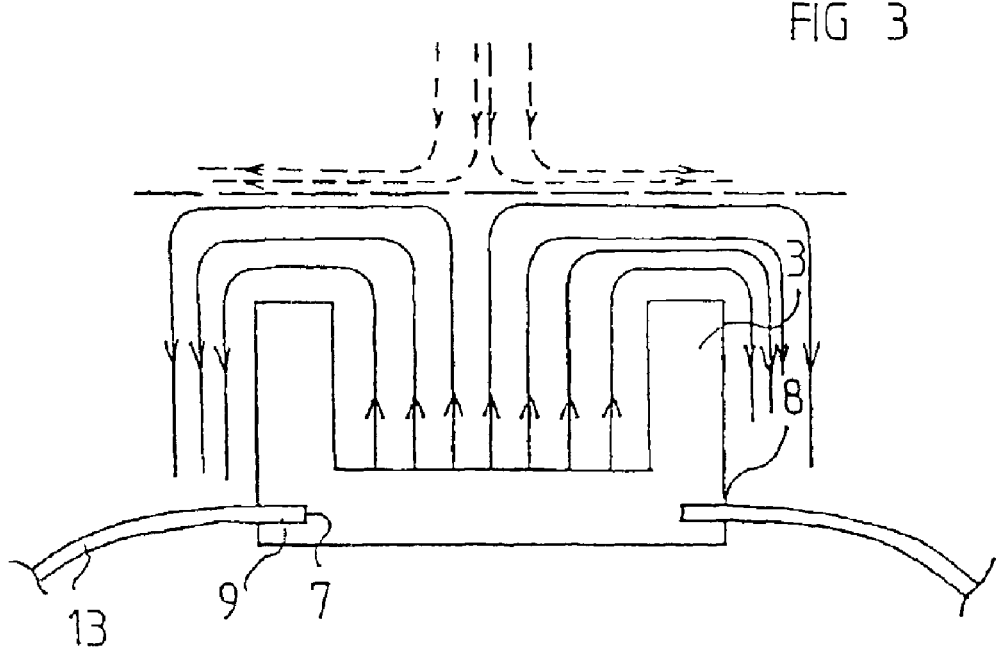

FIG. 4 discloses a device according to a second embodiment of the invention. As the device disclosed in FIG. 1, the device according to FIG. 4 includes a gas source (not disclosed) to which the supply conduit 1 (not disclosed) is connectable. In addition, the device includes a valve member (not disclosed) by which the gas supplied to the porous body 3 is controllable. According to this embodiment, the actual volume is defined by the porous body 3. As appears from FIG. 3, the porous body 3 has the shape of a container. In addition, the supply conduit 1 includes two substantially identical branches 13, each including a discharge end 7 and an end portion 9. In addition, the porous body 3 includes two holes 8, each being arranged to receive an end portion 9, which includes a discharge end 7 in one of said branches 13, and each being arranged to enclose the end portion of the actual branch 13. Both the holes 8 have a diameter which is somewhat less than the diameter of the actual end portion 9, wherein the end portions 9 are maintained in the holes 8 by means of friction. The gas is supplied through the supply conduit 1, the two branches 13 and through the porous body 3, wherein a gas cushion is formed, which substantially fills the volume defined by the container.

As appears from the arrows, indicating the gas flow from the porous body 3, the gas is supplied from the bottom of the container. The container may have such a size that sterilised instruments to be used during for instance an operation may be kept in the container. Hereby, the actual instruments are protected from bacteria and micro-organisms which may be present in the surrounding air. In the case that the gas supplied includes a substantial part of carbon dioxide, the bacteriostatic effect of carbon dioxide may also be utilised for preventing bacteria growth on instruments placed in the container.

Figure 5:
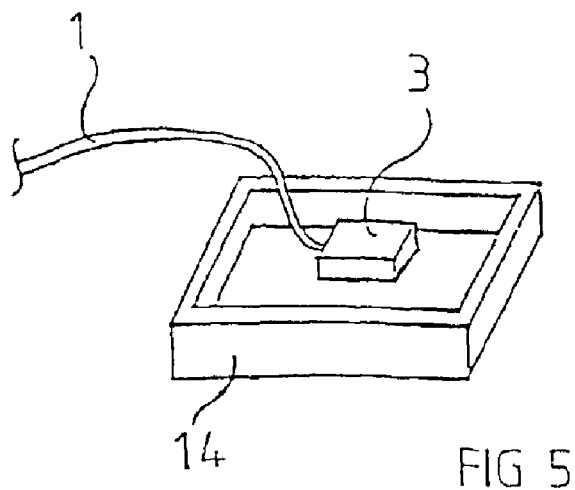

FIG. 5 discloses a normal container 14 manufactured, for instance, in a metal and in which instruments (not disclosed), that are used in connection with for instance an operation, may be placed. In order to prevent to as large an extent as possible, the instruments, especially when they are contaminated by blood, from contacting the surrounding air, a device of the type disclosed in FIG. 1 may be used. Consequently, the porous body 3 of a device of the type disclosed in FIG. 1 may be placed in the container 14, wherein a gas cushion is formed, which substantially fills the volume of the container 14. Hereby, surrounding air is prevented from contacting the actual instruments as long as the instruments are placed in the container 14.

In order to prevent air embolism, i.e. a blocking of the capillaries and small vessels, which may be caused by an air bubble, the protecting atmosphere in a volume adjoining a temporarily, outwardly open portion of a human being, ought to include a gas, the main component of which is carbon dioxide. As is mentioned previously reference is in this connection made to WO, A1, 99/29249. The advantage of using carbon dioxide in this connection is that carbon dioxide has a high solubility in tissue and may be permitted to penetrate into the open body portion and quickly be resorbed in the tissue. It is thus to be noted that the gas used in connection with the creation of a protecting atmosphere in a volume adjoining a temporarily open, inner portion of a human being as described in connection to FIG. 1, FIG. 2a and FIG. 2b, may include carbon dioxide. However, certain tissues are very oxygen dependent, wherein the gas in certain cases also should include a percentage of oxygen. It is possible to use the device described in connection with FIG. 3 in combination with the device described in connection with FIG. 1, FIG. 2a and FIG. 2b, in order to avoid, to an as large extent as possible, that the instruments, which are used in connection with the actual operation, contact the surrounding air. Hereby, it may be advantageous that the device described in connection with FIG. 4, uses air for creating the protecting atmosphere, in order to avoid that too much carbon dioxide are released in the surrounding air where persons are present. It is to be noted that the device described in connection with FIG. 5 also may include air for the same reason as being described above.

The present invention is not limited to the embodiments disclosed but may be varied and modified within the scope of the following claims.

What is claimed is:

1. A method for creating a protecting atmosphere in an outwardly open volume, including the steps of:
   providing a device, which is arranged to permit the supply of a gas and which includes at least one supply conduit including a flexible hose having a discharge end and a porous body provided at said discharge end and manufactured in a foam rubber-like material,
   positioning the porous body in the volume,
   supplying said gas to the volume by means of said device through the porous body and foam rubber-like material in such a way that a controlled, substantially laminar, continuous flow of said gas is formed, and
   providing said porous body in relation to said volume in such a way that the controlled gas flow forms a gas cushion, which substantially fills said volume, and that said gas cushion is arranged to prevent air from the environment from reaching said volume.

2. A method according to claim 1, wherein the porous body has such a design that the gas propagates in several directions from the body.

3. A method according to claim 1, wherein said porous body includes a homogenous body having a hole arranged to receive an end portion of said supply conduit, which includes said discharge end.

4. A method according to claim 3, wherein said hole extends to a point located substantially centrally in said homogenous body.

5. A method according to claim 4, wherein said hole has a diameter which substantially corresponds to the diameter of said end portion of said supply conduit.

6. A method according to claim 5, wherein said hole is arranged to surround said end portion of the supply conduit in such a way that said end portion is maintained in said hole by means of friction.

7. A method according to claim 1, wherein said porous body has a small size in relation to said volume.

8. A method according to claim 1, wherein said volume adjoins an outwardly open, inner portion of the body of a human being or an animal.

9. A method according to claim 8, wherein said porous body is provided in such a way that it abuts a part of said outwardly open, inner portion.

10. A method according to claim 1, wherein said volume is defined by the porous body.

11. A method according to claim 10, wherein said porous body forms the shape of the container.

12. A method according to claim 10, wherein the device includes means arranged to distribute the gas in said porous body.

13. A method according to claim 1, wherein the main component of the gas is carbon dioxide.

14. A method according to claim 1, wherein the gas includes approximately 10–20% oxygen.

15. A method according to claim 1, wherein the gas includes air.

16. A method according to claim 1, wherein at least a medicament is supplied to the gas to be discharged through the porous body.

17. A method according to claim 1, wherein the gas to be discharged through the porous body is conditioned.

18. A device arranged to create a protecting atmosphere in an outwardly open volume, said device comprising: a supply conduit, which is connectable to a gas source and which includes flexible hose having a discharge end and a porous body provided at said discharge end and manufactured in a foam rubber-like material, wherein the porous body is adapted to be positioned in the volume and wherein the device is arranged to supply the gas to said volume through the porous body and the foam rubber-like material, the porous body is arranged to supply the volume of said gas in a controlled, substantially laminar, continuous gas flow in order to enable the formation of a gas cushion intended to fill substantially said volume and thereby prevent air from the environment from reaching said volume.

19. A device according to claim 18, wherein the porous body is arranged to supply the gas in several directions from the body.

20. A device according to claim 18, wherein said porous body includes a homogenous body, which includes a hole arranged to receive an end portion of said supply conduit, which includes said discharge end.

21. A device according to claim 20, wherein said hole extends to a point located substantially centrally in said homogenous body.

22. A device according to claim 21, wherein said hole has a diameter, which substantially corresponds to the diameter of said end portion of said supply conduit.

23. A device according to claim 22, wherein said hole is arranged to surround said end portion of the supply conduit in such a way that said end portion is maintained in said hole by means of friction.

24. A device according to claim 18, wherein said volume adjoins an outwardly open, inner portion of the body of a human being or an animal and wherein said body is arranged to be provided, during the creation of said atmosphere, in such a way that it abuts a part of said outwardly open, inner portion.

25. A device according to claim 18, wherein said supply conduit is manufactured of a flexible material.

* * * * *